United States Patent
Schlesinger et al.

(10) Patent No.: US 12,173,326 B2
(45) Date of Patent: Dec. 24, 2024

(54) CELL CULTURE MEDIA AND METHODS FOR GENERATING HUMAN ALVEOLAR MACROPHAGE-LIKE CELLS

(71) Applicant: TEXAS BIOMEDICAL RESEARCH INSTITUTE, San Antonio, TX (US)

(72) Inventors: Larry S. Schlesinger, San Antonio, TX (US); Susanta Pahari, San Antonio, TX (US)

(73) Assignee: TEXAS BIOMEDICAL RESEARCH INSTITUTE, San Antonio, TX (US)

( * ) Notice: Subject to any disclaimer, the term of this patent is extended or adjusted under 35 U.S.C. 154(b) by 0 days.

(21) Appl. No.: 17/657,344

(22) Filed: Mar. 30, 2022

(65) Prior Publication Data
US 2022/0315900 A1    Oct. 6, 2022

Related U.S. Application Data

(60) Provisional application No. 63/200,810, filed on Mar. 30, 2021.

(51) Int. Cl.
*C12N 5/071* (2010.01)

(52) U.S. Cl.
CPC ........ *C12N 5/0688* (2013.01); *C12N 2501/15* (2013.01); *C12N 2501/22* (2013.01); *C12N 2501/231* (2013.01); *C12N 2506/115* (2013.01)

(58) Field of Classification Search
None
See application file for complete search history.

(56) References Cited

PUBLICATIONS

Hussel et al. Alveolar macrophages: plasticity in a tissue-specific context (2014) Nature Reviews Immunology, 14, pp. 81-93. (Year: 2014).*
Willson et al. Effect of Exogenous Surfactant (Calfactant) in Pediatric Acute Lung Injury (2005) JAMA, 293. (Year: 2005).*
Arora et al. Cell Culture Media: A Review (2013) Mater Methods, 3. (Year: 2013).*
Yu et al. The Cytokine TGF-b Promotes the Development and Homeostasis of Alveolar Macrophages (2017) Immunity, 47, pp. 903-912. (Year: 2017).*
Geertsma et al. Monocytes incubated with surfactant: a model for human alveolar macrophages? (1997) Journal of Leukocyte Biology, 62, pp. 485-492. (Year: 1997).*
Gantner et al. In vitro dierentiation of human monocytes to macrophages: change of PDE pro® le and its relationship to suppression of tumour necrosis factor—a release by PDE inhibitors (1997) British Journal of Pharmacology, 121, pp. 221-231. (Year: 1997).*

* cited by examiner

*Primary Examiner* — Kara D Johnson
*Assistant Examiner* — Maytee Marie Contes De Jesus
(74) *Attorney, Agent, or Firm* — Womble Bond Dickinson (US) LLP (57) ABSTRACT

Provided here methods of generating human alveolar macrophage-like cells in-vitro from blood-derived monocytes by culturing them in a cell culture medium containing a mixture of a surfactant and two or more cytokines. This mixture can contain calfactant, granulocyte-macrophage colony-stimulating factor, transforming growth factor beta, and interleukin-10.

9 Claims, 13 Drawing Sheets
(4 of 13 Drawing Sheet(s) Filed in Color)

FIG. 1

Shortlisted gene signature to differentiate MDM and HAM

| SL No | Genes | MDM 2hr average RPM value | HAM 2hr average RPM value |
|---|---|---|---|
| 1 | IL8 | 102.508 | 5876.536 |
| 2 | CD74 | 419.890 | 3217.007 |
| 3 | DUSP1 | 72.195 | 2810.896 |
| 4 | HLA-DPB1 | 146.840 | 2041.311 |
| 5 | OLR1 | 49.113 | 1881.111 |
| 6 | MRC1 | 373.582 | 1846.700 |
| 7 | C19orf59/MCEMP1 | 1.958 | 1501.346 |
| 8 | PPP1R15A | 72.002 | 1326.457 |
| 9 | EGR1 | 9.161 | 1220.729 |
| 10 | FOSB | 1.865 | 1214.796 |
| 11 | ATF4 | 189.284 | 1066.257 |
| 12 | CES1 | 0.759 | 993.768 |
| 13 | TNF | 4.878 | 951.032 |
| 14 | NFKBIA | 109.594 | 925.296 |
| 15 | MARCO | 27.584 | 913.371 |
| 16 | HLA-DQA1 | 14.946 | 904.718 |
| 17 | CXCL3 | 5.762 | 783.711 |
| 18 | SERPING1 | 57.754 | 775.500 |
| 19 | CCL18 | 3.287 | 768.543 |
| 20 | HSPB1 | 156.307 | 741.189 |
| 21 | PPARG | 56.132 | 737.089 |
| 22 | CXCL5 | 4.263 | 621.929 |
| 23 | ZFP36 | 69.416 | 578.232 |
| 24 | MCL1 | 85.064 | 524.593 |
| 25 | ITGAX | 132.496 | 567.474 |
| 26 | MMP9 | 7163.543 | 104.429 |
| 27 | TM4SF19 | 2476.417 | 88.157 |
| 28 | CD84 | 930.914 | 82.818 |
| 29 | CCL22 | 2234.179 | 66.475 |
| 30 | CD36 | 670.785 | 41.468 |
| 31 | MMP12 | 1354.814 | 2.557 |
| 32 | MMP7 | 2357.513 | 2.286 |
| | Black color shows higher expression in HAM | | |
| | Blue color shows higher expression in MDM | | |

FIG. 6A    FIG. 6B    FIG. 6C    FIG. 6D    FIG. 6E FIG. 6F    FIG. 6G    FIG. 6H    FIG. 6I    FIG. 6J FIG. 6K    FIG. 6L    FIG. 6M    FIG. 6N    FIG. 6O

CELL CULTURE MEDIA AND METHODS FOR GENERATING HUMAN ALVEOLAR MACROPHAGE-LIKE CELLS

CROSS-REFERENCE TO RELATED APPLICATIONS

This application claims the benefit of and priority to U.S. Provisional Application No. 63/200,810, filed on Mar. 30, 2021, which is incorporated by reference herein in its entirety.

GOVERNMENT SUPPORT

This invention was made with government support under Grant Number R01AI136831 awarded by National Institutes of Health. The government has certain rights in the invention.

TECHNICAL FIELD

The disclosure relates generally to the field of cell culture media and systems and methods for generating, culturing, or maintaining human alveolar macrophage-like cells.

BACKGROUND

Human alveolar macrophages (HAM) are unique lung-resident macrophages and are often the first cell type to come into contact with invading airborne pathogens. They also critically impact a variety of lung inflammatory processes and diseases. The contribution of HAM during pulmonary diseases is poorly understood due to the difficulty in accessing HAM from human donors. One method of acquiring HAM is from bronchoalveolar lavage, an expensive and labor intensive process. Another method is to obtain HAM from lung tissue of recently deceased individuals and this method is available to only a few labs. Further challenges are posed by the rapid phenotypic changes of HAM that occur during in vitro culture. Therefore, obtaining HAM can be prohibitive in terms of resources for commercial cell assays.

SUMMARY

There remains an unmet need for cost effective methods for generation, culturing, maintenance, and/or expansion of primary cells to a HAM phenotype. Alveolar surfactant components and specific cytokines present in the alveolar space with respect to the development and maintenance of HAM were analyzed. Embodiments include systems and methods for generating, culturing, or maintaining HAM-like cells. Embodiments include cell culture media for generating human alveolar macrophage-like (AML) cells from blood-derived monocytes. Certain embodiments of the culture media include a cocktail of one or more surfactants and one or more cytokines to develop human AML cells that retain their HAM phenotype and function in tissue culture. Embodiments include certain culture conditions that facilitate the conversion of blood-obtained monocytes to a HAM phenotype. Embodiments include methods of generating human AML cells in-vitro from blood-derived monocytes. One such method includes culturing a population of blood-derived monocytes in a cell culture medium containing a mixture of a surfactant and two or more cytokines.

In certain embodiments, the cell culture medium contains a basal medium; and a mixture of a surfactant and two or more cytokines. In certain embodiments, the surfactant is calfactant. The calfactant can be present at about 100 µg/mL. In certain embodiments, the cytokines are two or more of a granulocyte-macrophage colony-stimulating factor (GM-CSF), a transforming growth factor beta (TGF-β), and an interleukin 10 (IL-10). Certain embodiments of the culture media include a surfactant and three cytokines in vitro to develop AML cells that retain their HAM phenotype and function in tissue culture.

In certain embodiments, the cell culture medium contains GM-CSF or a GM-CSF family member or variants or functional fragments thereof. The GM-CSF or a GM-CSF family member or variants or functional fragments thereof can be present in the cell culture medium at concentrations ranging from about 0.5 ng/ml to about 120 ng/ml. In certain embodiments, the cell culture medium contains TGF-β or a TGF-β family member or variants or functional fragments thereof. The TGF-β or a TGF-β family member or variants or functional fragments thereof can be present in the cell culture medium at concentrations ranging from about 0.5 ng/ml to about 120 ng/ml. In certain embodiments, the cell culture medium contains IL-10 or an IL-10 family member or variants or functional fragments thereof. The IL-10 or an IL-10 family member or variants or functional fragments thereof can be present in the cell culture medium at concentrations ranging from about 0.5 ng/ml to about 120 ng/ml. In certain embodiments, the cell culture medium contains GM-CSF at about 10 ng/mL, the TGF-β is present at about 5 ng/mL, and the IL-10 at about 5 ng/mL.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments will be readily understood by the following detailed description in conjunction with the accompanying drawings. Embodiments are illustrated by way of example and not by way of limitation in the accompanying drawings.

FIG. 4 is a photographic image of Western blots of untreated MDM cells (UT-MDM) and AML cells demonstrating HAM like phenotype. There was an increased expression of PPARG, transcription factor PU.1, H3K4me1 (Histone H3 monomethylated at lysine 4) and decreased expression of H3K4me3 (Histone H3 trimethylated at lysine 4). Actin was used as a loading control. Representative data showing the expression of indicated proteins from three human donors.

DETAILED DESCRIPTION

HAM is the first line of defense against any invading respiratory pathogens. HAM is critical for tissue homeostasis, host defense, clearance of surfactant and cell debris, pathogen recognition, initiation and resolution of lung inflammation, and repair of damaged tissue. However, in respiratory diseases including chronic obstructive pulmonary disease (COPD), asthma, and cystic fibrosis, and infectious diseases like tuberculosis and COVID-19, HAM appears to be dysfunctional and may contribute to disease pathogenesis. Conducting research on HAM is extremely difficult.

The present disclosure describes various embodiments of compositions, methods, and systems to generate, culture, and/or maintain cells with a human HAM phenotype (AML cells). In certain embodiments, the AML cells are generated from blood-derived monocytes cultured in specific cell culture media. Embodiments also include cell culture media containing a cocktail of one or more surfactants and one or more cytokines to develop human AML cells that retain their HAM phenotype and function in tissue culture. In the following description, numerous details are set forth in order to provide a thorough understanding of the various embodiments. Before the present methods and compositions are described in detail, it is to be understood that these embodiments are not limited to particular methods or compositions described, as such may, of course, vary. It is also to be understood that the terminology used herein is for the purpose of describing particular embodiments only, and is not intended to be limiting, as the scope of the present embodiments will be limited only by the appended claims. The description may use the phrases "in certain embodiments," "in various embodiments," "in an embodiment," or "in embodiments," which may each refer to one or more of the same or different embodiments. Furthermore, the terms "comprising," "including," "having," and the like, as used with respect to embodiments of the present disclosure, are synonymous.

Embodiments include systems and methods for generating, culturing, or maintaining HAM-like cells. Embodiments include cell culture media for generating human AML cells from blood-derived monocytes. In certain embodiments, the cell culture medium contains a basal medium and a mixture of a surfactant and two or more cytokines.

In certain embodiments, the surfactant is calfactant. The calfactant can be present at about 100 µg/mL. In certain embodiments, the cytokines in the cell culture medium include one or more of a granulocyte-macrophage colony-stimulating factor (GM-CSF), a transforming growth factor beta (TGF-β), and an interleukin 10 (IL-10). Certain embodiments of the culture media include a surfactant and three cytokines in vitro to develop human AML cells that retain their HAM phenotype and function in tissue culture.

In certain embodiments, the cell culture medium contains GM-CSF or a GM-CSF family member or variants or functional fragments thereof. As used herein, the term "member of the GM-CSF family" or the like refers to growth factors that are generally characterized by one of skill in the art as belonging to the GM-CSF family, either due to homology with known members of the GM-CSF family, or due to similarity in function with known members of the GM-CSF family. GM-CSF or a GM-CSF family member or variants or functional fragments thereof can be present in the cell culture medium at concentrations ranging from about 0.5 ng/ml to about 120 ng/ml. In some embodiments, GM-CSF or a GM-CSF family member or variants or functional fragments thereof can be present in the cell culture medium at concentrations ranging from about 1 ng/ml to about 100 ng/ml. In some embodiments, GM-CSF or a GM-CSF family member or variants or functional fragments thereof can be present in the cell culture medium at concentrations ranging from about 1 ng/ml to about 50 ng/ml. In some embodiments, GM-CSF or a GM-CSF family member or variants or functional fragments thereof can be present in the cell culture medium at concentrations ranging from about 1 ng/ml to about 20 ng/ml. In some embodiments, GM-CSF or a GM-CSF family member or variants or functional fragments thereof can be present in the cell culture medium at concentrations ranging from about 5 ng/ml to about 20 ng/ml.

In certain embodiments, the cell culture medium contains TGF-β or a TGF-β family member or variants or functional fragments thereof. As used herein, the term "member of the TGF-β family" or the like refers to growth factors that are generally characterized by one of skill in the art as belonging to the TGF-β family, either due to homology with known members of the TGF-β family, or due to similarity in function with known members of the TGF-β family. TGF-β or a TGF-β family member or variants or functional fragments thereof can be present in the cell culture medium at concentrations ranging from about 0.5 ng/ml to about 120 ng/ml. In some embodiments, TGF-β or a TGF-β family member or variants or functional fragments thereof can be present in the cell culture medium at concentrations ranging from about 1 ng/ml to about 100 ng/ml. In some embodiments, TGF-β or a TGF-β family member or variants or functional fragments thereof can be present in the cell culture medium at concentrations ranging from about 1 ng/ml to about 50 ng/ml. In some embodiments, TGF-β or a TGF-β family member or variants or functional fragments thereof can be present in the cell culture medium at concentrations ranging from about 1 ng/ml to about 20 ng/ml. In some embodiments, TGF-β or a TGF-β family member or variants or functional fragments thereof can be present in the cell culture medium at concentrations ranging from about 1 ng/ml to about 10 ng/ml.

In certain embodiments, the cell culture medium contains IL-10 or an IL-10 family member or variants or functional fragments thereof. As used herein, the term "member of the IL-10 family" or the like refers to growth factors that are generally characterized by one of skill in the art as belonging to the IL-10 family, either due to homology with known members of the IL-10 family, or due to similarity in function with known members of the IL-10 family. IL-10 or an IL-10 family member or variants or functional fragments thereof can be present in the cell culture medium at concentrations ranging from about 0.5 ng/ml to about 120 ng/ml. In some embodiments, IL-10 or an IL-10 family member or variants or functional fragments thereof can be present in the cell culture medium at concentrations ranging from about 1 ng/ml to about 100 ng/ml. In some embodiments, IL-10 or an IL-10 family member or variants or functional fragments thereof can be present in the cell culture medium at concentrations ranging from about 1 ng/ml to about 50 ng/ml. In some embodiments, IL-10 or an IL-10 family member or variants or functional fragments thereof can be present in the cell culture medium at concentrations ranging from about 1 ng/ml to about 20 ng/ml. In some embodiments, IL-10 or an IL-10 family member or variants or functional fragments thereof can be present in the cell culture medium at concentrations ranging from about 1 ng/ml to about 10 ng/ml.

The systems and methods described herein can be used for the purposes of studying or examining pharmacology, toxicology, drug development, drug delivery, drug metabolism, drug-drug interaction drug bioavailability, drug clearance, multi-organ interactions, diagnostics, therapeutics, nutritional applications, physiology of the lung, respiratory disease models and their mechanism, and etiology of disease in the respiratory system.

Embodiments include a cell culture medium for developing human alveolar macrophage-like (AML) cells which exhibit human alveolar macrophage phenotype and function. This cell culture medium contains a basal medium and a mixture of one or more surfactants and two or more cytokines. Basal media contain amino acids, glucose, and ions (such as one or more of calcium, magnesium, potassium, sodium, and phosphate) essential for cell survival and growth. Examples of basal media include but are not limited to Eagle's minimum essential medium (MEM), Dulbecco's Modified Eagle's Medium (DMEM or DMEM F12), alpha-Minimum Essentials Medium (a-MEM), 199 medium, RPMI-1640, L-15, Hum F-10 and Hum F-12, DM-160 and DM-170. The composition of the basal medium can be customized to the particular cells that form the starting material.

Suitable surfactants include, but are not limited to, natural and synthetic surfactant preparations having the function of natural pulmonary surfactant. These surfactants can contain phospholipids and/or pulmonary surfactant proteins. The surfactants can be provided as individual components or as extracts from biological sources, such as non-human animals. For example, the surfactant composition can be an extract of natural surfactant from calf lungs, which includes phospholipids, neutral lipids, and hydrophobic surfactant-associated proteins B and C (SP-B and SP-C). In an embodiment, the surfactant is calfactant. As used here, calfactant is a product derived from the natural surfactant in calf lungs. For example, the Infasurf® calfactant is an extract of natural surfactant from calf lungs suspended in 0.9% saline. Each milliliter of a commercially sold Infasurf® product contains 35 mg of phospholipids (including 26 mg phosphatidylcholine of which 16 mg is disaturated phosphatidylcholine) and 0.65 mg of proteins including surfactant-associated proteins B and C. In an embodiment, the calfactant is present at about 100 μg/mL. Other examples of surfactants include one or more surfactants prepared, extracted, or derived from porcine lungs or bovine lungs. Other suitable surfactants include compounds obtained from natural sources, such as pulmonary lavage or extraction from amniotic fluid, and proteins prepared by genetic engineering or chemical synthesis. Surfactants compositions can include SP-B and SP-C and their modified derivatives, including recombinant forms of the proteins.

In an embodiment, the cytokines include two or more of granulocyte-macrophage colony-stimulating factor (GM-CSF), transforming growth factor beta (TGFβ), and interleukin 10 (IL-10). In an embodiment, the GM-CSF is present at about 10 ng/mL, the TGFβ is present at about 5 ng/mL, and the IL-10 is present at about 5 ng/mL. Embodiments include a method of promoting AML cell generation and expansion in-vitro. One aspect of the method includes culturing a population of blood-derived monocytes in a cell culture medium containing a mixture of one or more surfactants and two or more cytokines. Another aspect of the method includes culturing a population of blood-derived monocytes in a cell culture medium containing a mixture of calfactant, GM-CSF, TGFβ, and IL-10. In an embodiment, the calfactant is present at about 100 g/mL, the GM-CSF at about 10 ng/mL, the TGFβ at about 5 ng/mL, and the IL-10 at about 5 ng/mL.

In certain embodiments, the method for generating and/or culturing AML cells includes supplying a population of blood-derived monocytes to a cell culture container, treating this population of cells with a cell culture medium, containing a mixture of one or more surfactants and two or more cytokines, on a periodic basis under conditions to promote cell differentiation, eliminating the non-adherent cells from the cell culture container by washing, or changing the cell culture medium to generate the AML cells. These AML cells are present as cells adhered to the walls of the cell culture container. In an embodiment, the AML cells can be harvested and seeded into other cell culture containers for carrying out experiments. The cell culture containers vary in size, shape, and materials.

HAMs are unique lung-resident macrophages responsible for maintaining lung homeostasis, clearing debris and surfactant, and are often the first cell type to come into contact with invading pathogens and environmental particulates. Because of their location and unique phenotype, they play a central role in lung inflammatory processes and repair. MDM are hematopoietic cells, derived from monocytes in the blood, and are recruited to tissue sites including the lung but are distinct in their biology from HAM. In humans, it has been demonstrated that these two macrophage subsets possess distinct transcriptional profiles and generally respond differently to infectious diseases. In the laboratory, MDM models are more commonly used than HAM models, in large part due to the abundancy and ease of obtaining human monocytes compared to HAM. HAM can only be obtained by bronchoalveolar lavage (BAL) or from tissue of deceased individuals and their phenotype rapidly changes during ex vivo tissue culture conditions. As MDM do not behave the same as HAM during infection, it is difficult to truly understand the contribution of HAM during pulmonary diseases in humans.

Certain embodiments include a culture system that allows for blood-derived monocytes to be converted to a HAM phenotype for in vitro studies. Embodiments also include cell media containing the surfactant components and specific cytokines present in the alveolar space for the development and homeostasis of HAM. The systems described here mimic the alveolar environment in cell culture for in vitro development of HAM. In an embodiment, the cell media contains calfactant, which is a lung surfactant formulation that helps to prevent and treat respiratory distress syndrome in newborns, to restore surface activity in the lungs, and to improve respiration. GM-CSF, TGF-β, and IL-10 are lung associated cytokines that play an important role in the development of HAM in vivo. In an embodiment, a cocktail of a surfactant (Infasurf®: 100 g/mL) and cytokines (GM-CSF: 10 ng/mL, TGFβ: 5 ng/mL, IL-10: 5 ng/mL) (AM-L_ALL treated) was used to generate and maintain AML cells in vitro, which exhibit AM phenotype and function.

Figure 1:
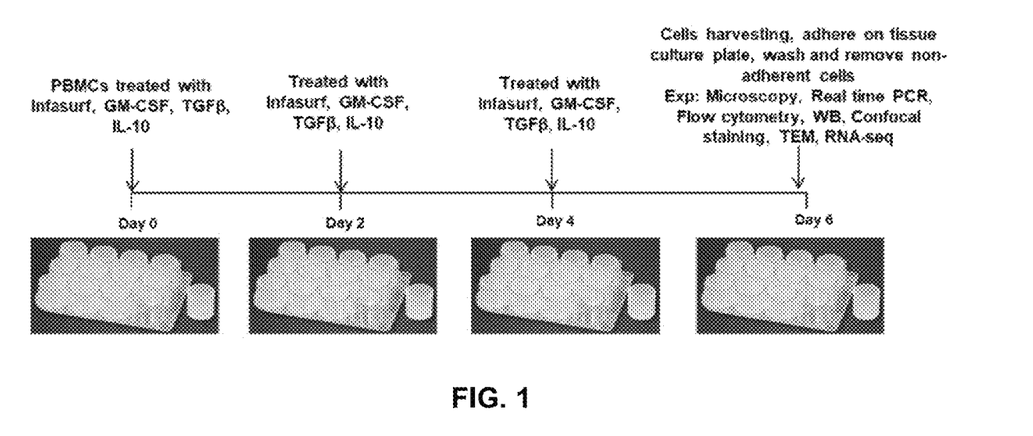
FIG. 1 is a representative image of a method to differentiate peripheral blood monocyte-derived macrophages (MDM) and AML cells, according to an embodiment.

One method of generating the AML cells includes placing human normal peripheral blood mononuclear cells (PBMCs) in a cell culture container, treating the PBMCs with a cell culture medium containing a mixture of one or more surfactants and two or more cytokines on a periodic basis, and isolating the cells adherent to the walls of the cell culture container. The method also includes removing the non-adherent cells by washing, or by changing the cell culture medium. FIG. 1 is a representative image of a method to differentiate peripheral blood MDM and AML cells, according to an embodiment. Healthy human PBMCs were exposed (Day 0, Day 2, Day 4) to lung associated components for 6 days. The cells were treated with surfactant (Infasurf®) and cytokines (GM-CSF, TGF-β, IL-10) every alternative day, or left untreated (UT-MDM). The cells were harvested and plated in cell culture plate for 2 hours. The non-adherent cells were removed. The adherent cells were collected for microscopy, real time PCR, flow cytometry, WB, confocal staining, TEM, and RNA-seq.

Figure 2:
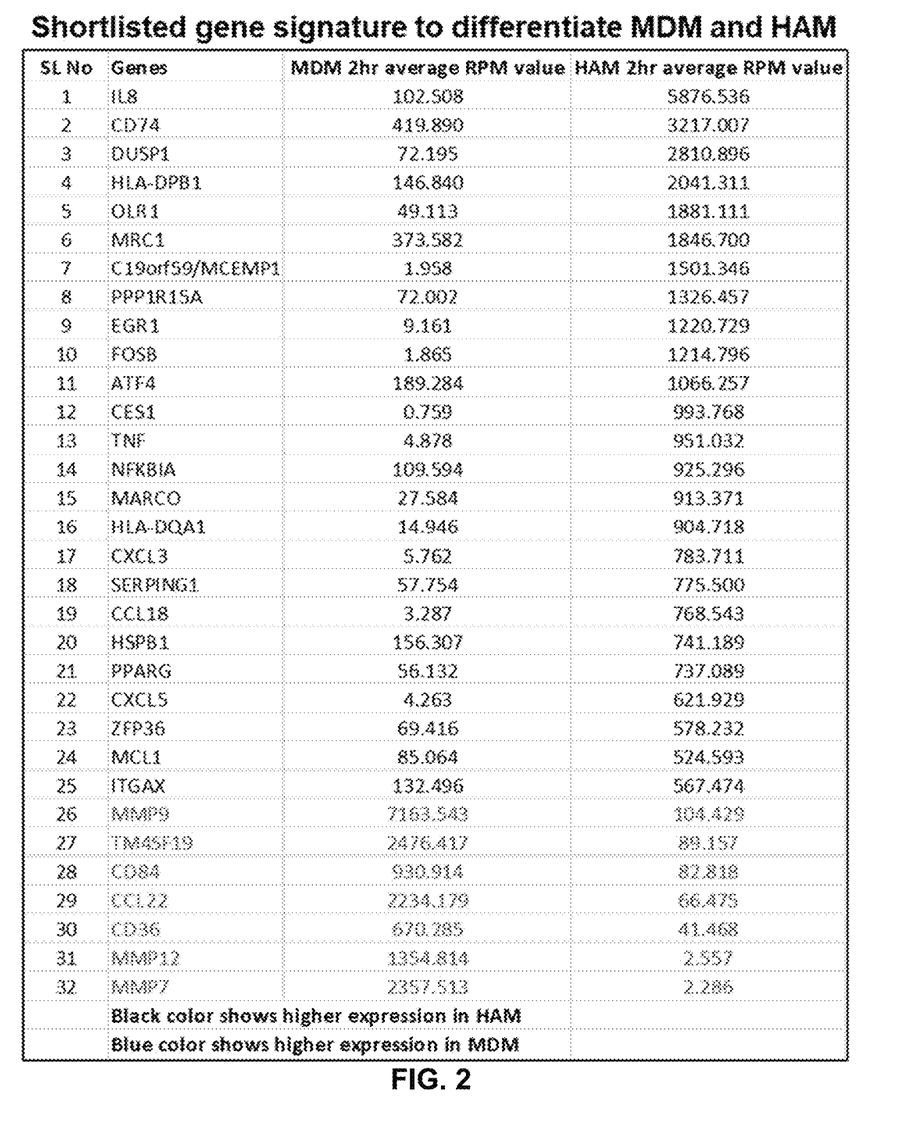
FIG. 2 is a tabular presentation of a shortlisted gene signature to differentiate MDM and HAM cells.
Figure 3A:
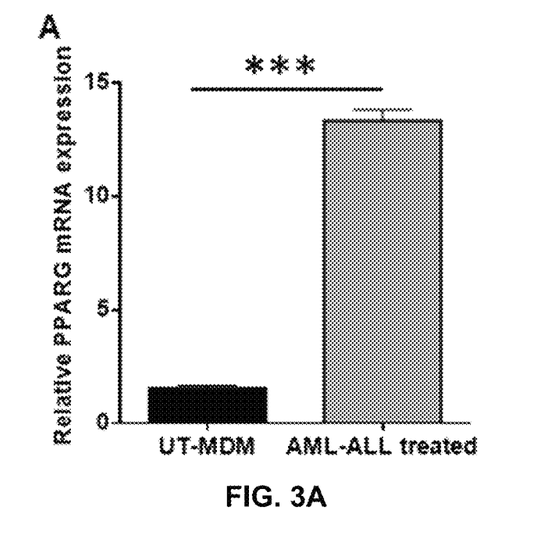
FIGS. 3A-3P are graphical representations of qRT-PCR data of demonstrating significant increases in PPARG (FIG. 3A), MRC1 (FIG. 3B), MARCO (FIG. 3C), MERTK (FIG. 3D), CES1(FIG. 3E), CD170 (FIG. 3F), MCEMP1 (FIG. 3G), MCL 1 (FIG. 311), CCL 18 (FIG. 3I), CXCL3 (FIG. 3J), DUSP1 (FIG. 3K), CXCL5 (FIG. 3L), CD36 (FIG. 3M), MMP7 (FIG. 3N), MMP9 (FIG. 3O), and CCL22 (FIG. 3P) expression in AML cells (ALL cocktail treated) as compared to untreated MDM (UT-MDM). All gene expressions are normalized to Actin. Representative bar diagram showing the relative mRNA expression of indicated genes from 8 human donors.
Figure 3B:
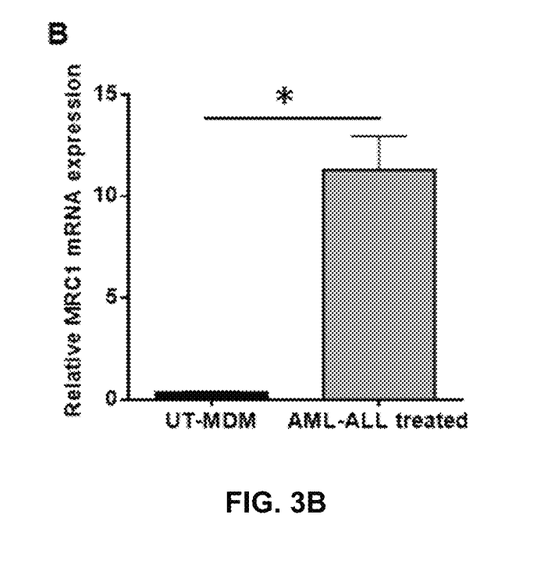
Figure 3C:
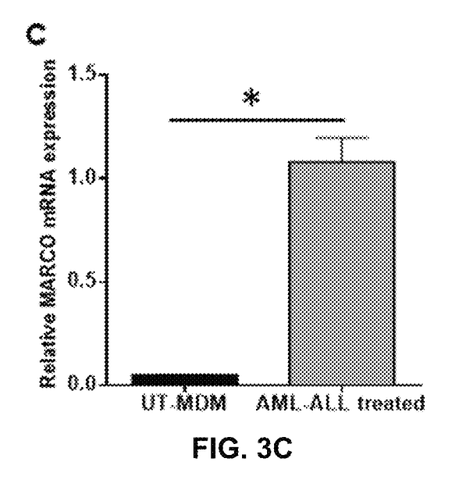
Figure 3D:
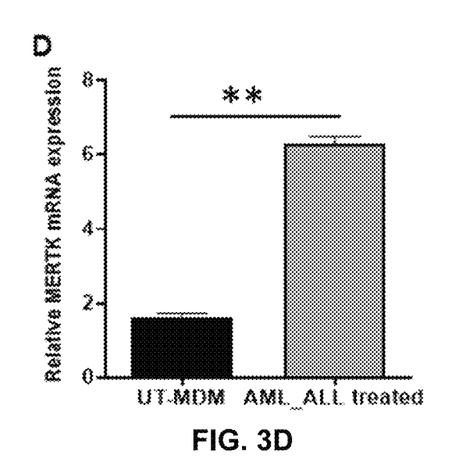
Figure 3E:
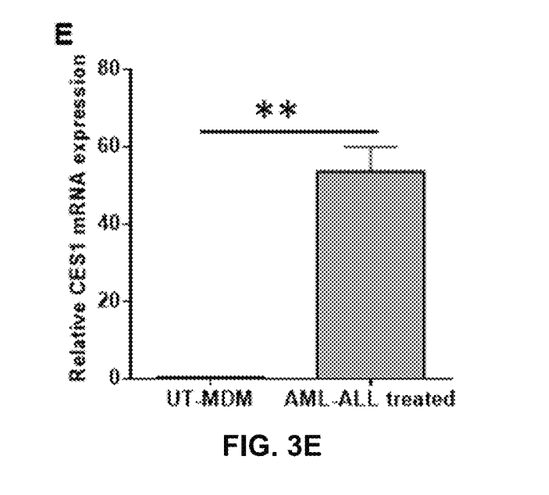
Figure 3F:
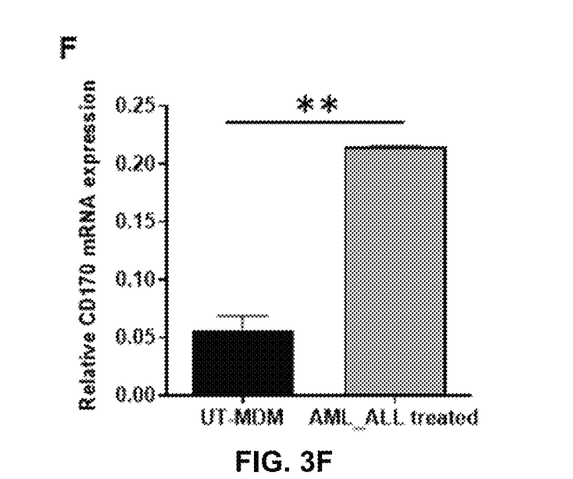
Figure 4:
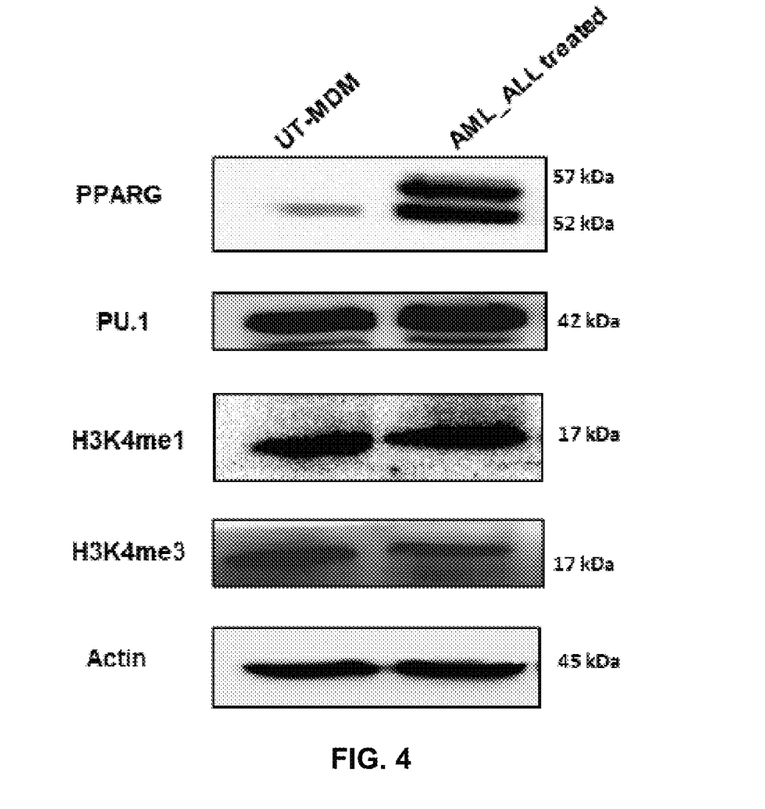

To assess the phenotype and function of AML cells, a list of 32 genes were developed to serve as a signature to differentiate HAM and MDM (FIG. 2). These genes were assessed in the untreated-MDM (UT-MDM) with AML (ALL treated) cells by qRT-PCR. The AML (ALL treated) cells show a HAM like phenotype, with increased expression of genes that are highly expressed in HAM. There were substantial increases in PPARG (peroxisome proliferator activated receptor gamma), MRC1 (C-type mannose receptor 1), MARCO (macrophage receptor with collagenous structure), MERTK (mer tyrosine kinase), CES1 (Carboxylesterase 1), CD170, and other gene expression in AML cells as compared to untreated MDM (UT-MDM) (FIG. 3A-3F). Expression of a few genes which are highly expressed in MDM but not in HAM were also assessed. These genes were down-regulated in AML cells (FIGS. 2 and 3). The expression of PPARG, PU.1, H3K4mel, and H3K4me3 were evaluated by Western blot. Increased expression of PPARG, PU.1, H3K4mel and decreased expression of H3K4me3 shows HAM like phenotype (FIG. 4). Further, all these data were validated at the protein level by confocal microscopy, and flow cytometry for selected proteins (CD200R, CD11c, MRC1/CD206, CD163, CD170 expression) which are highly expressed in HAM and also in AML cells (FIGS. 5A-5O and FIGS. 6A-6O).

The transcriptomic analysis was assessed from MDM and HAM cells after 2-hour adherence in culture. FIG. 2 is a shortlisted gene signature to differentiate MDM and HAM and was used to compare with AML cells. These are the 32 shortlisted gene signatures in MDM and HAM cells. These genes are selected based on their abundancy in HAM relative to MDM and a previously generated AmpliSeq data base comparing MDM and HAM transcriptomes (Publication titled, "AmpliSeq transcriptome analysis of human alveolar and monocyte-derived macrophages over time in response to *Mycobacterium tuberculosis* infection" by Audrey C Papp and Abul K Azad et al., PLoS One. (2018)). "RPM" means "reads per million" that is determined by calculating how many reads map to the gene of interest, dividing it by the total number of aligned reads, and multiplying by one million. These genes were assessed by qRT-PCR, comparing untreated-MDM (UT-MDM) with AML (ALL treated) cells.

Figure 3G:
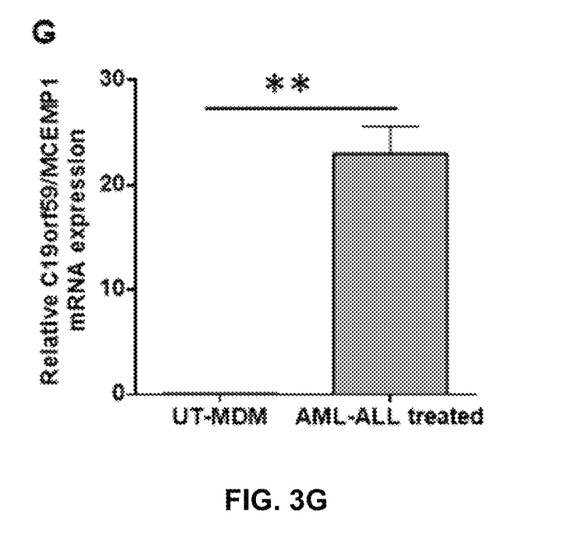
Figure 3H:
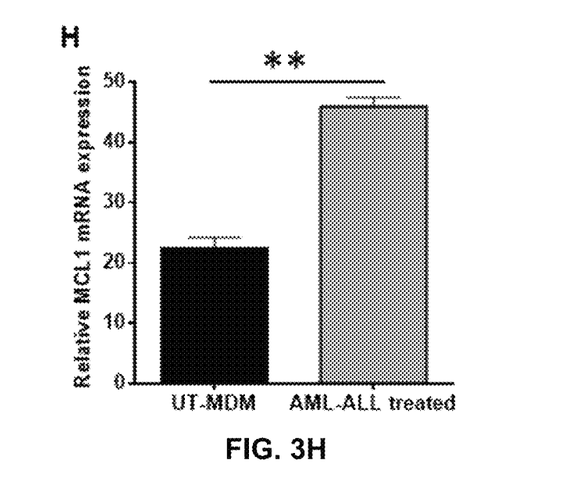
Figure 3I:
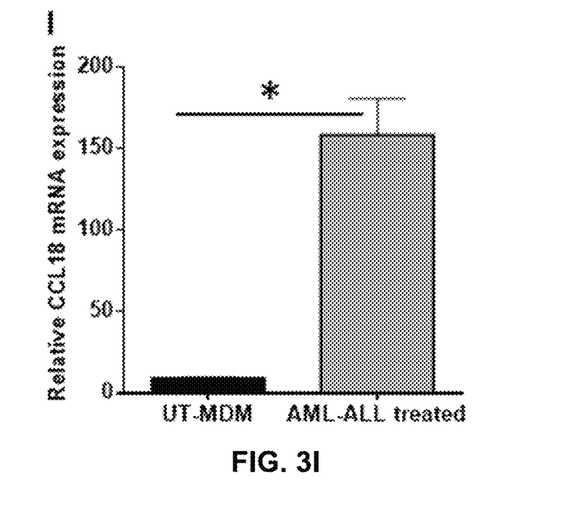
Figure 3J:
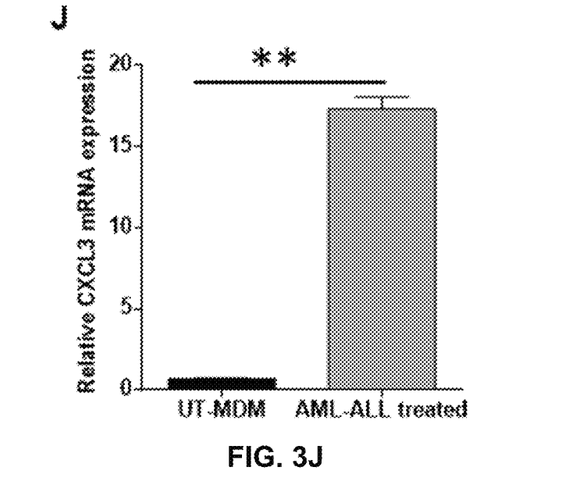
Figure 3K:
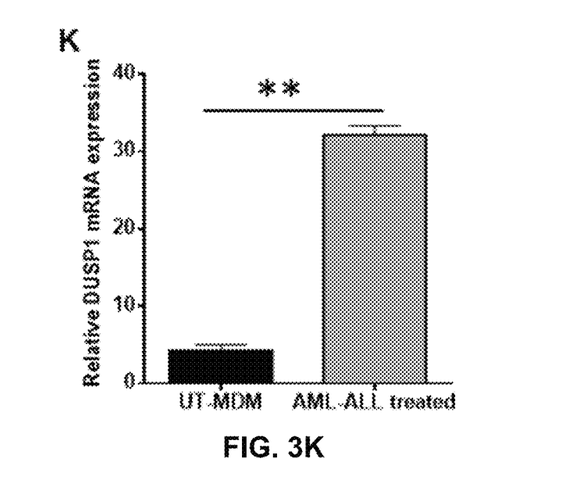
Figure 3L:
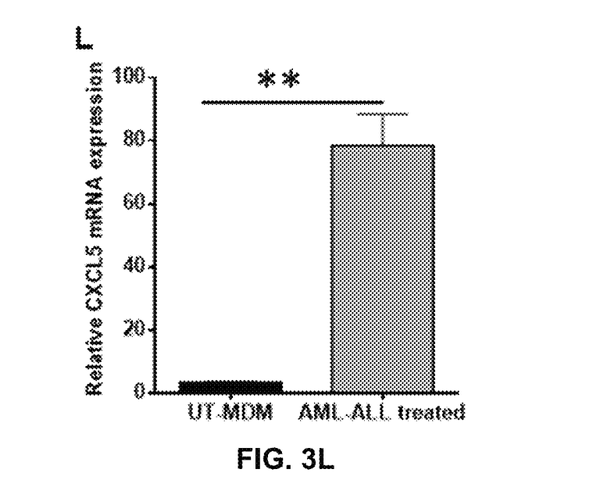
Figure 3M:
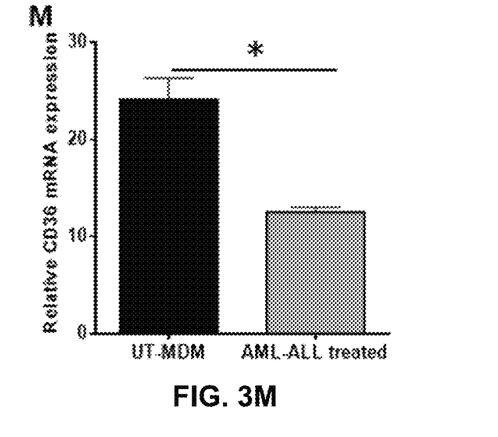
Figure 3N:
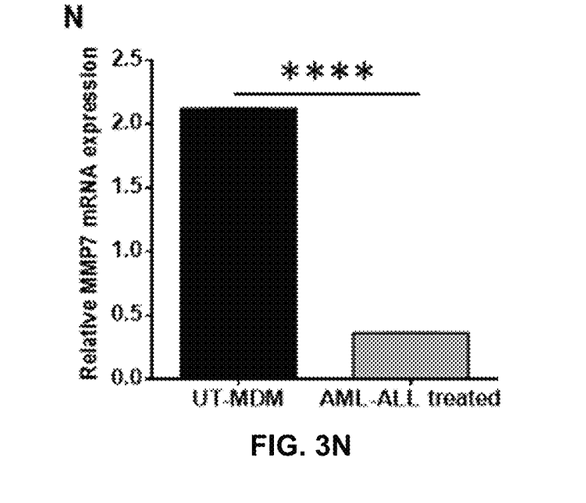
Figure 3O:
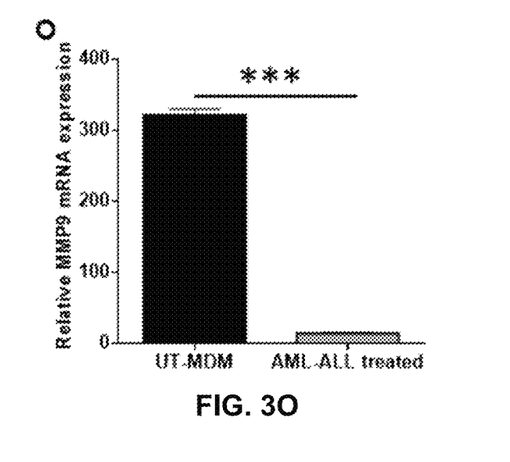
Figure 3P:
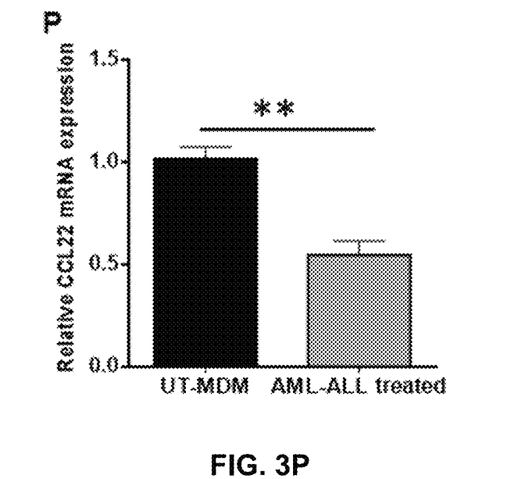

Healthy human PBMCs were exposed to lung associated components for 6 days (treated with ALL cocktail of surfactant and cytokines every alternative day, or left untreated (UT-MDM)). The AML cells exhibited a similar phenotype to HAM. The qRT-PCR data demonstrate significant increases in PPARG, MRC1, MARCO, MERTK, CES1, CD170, MCEMP1, MCL 1, CCL 18, CXCL3, DUSP1, CXCL5, CD36, MMP7, MMP9, and CCL22 expression in AML cells (ALL cocktail treated) as compared to untreated MDM (UT-MDM) (FIG. 3A-P). FIG. 3A-3P are graphical representations of qRT-PCR data of demonstrating significant increases in PPARG (FIG. 3A), MRC1 (FIG. 3B), MARCO (FIG. 3C), MERTK (FIG. 3D), CES1(FIG. 3E), CD170 (FIG. 3F), MCEMP1 (Mast Cell Expressed Membrane Protein 1) (FIG. 3G), MCL 1 (Myeloid cell leukemia-1) (FIG. 3H), CCL 18 (C-C Motif Chemokine Ligand 18) (FIG. 3I), CXCL3 (Chemokine (C-X-C motif) ligand 3) (FIG. 3J), DUSP1 (Dual Specificity Phosphatase 1) (FIG. 3K), CXCL5 (C-X-C Motif Chemokine Ligand 5) (FIG. 3L), CD36 (FIG. 3M), MMP7 (FIG. 3N), MMP9 (Matrix Metallopeptidase 7) (FIG. 3O), and CCL22 (C-C Motif Chemokine Ligand 22) (FIG. 3P) expression in AML cells (ALL cocktail treated) as compared to untreated MDM (UT-MDM). All gene expressions are normalized to Actin. Representative bar diagram showing the relative mRNA expression of indicated genes from 8 human donors.

Next, the AML cells were assessed for HAM like phenotype. Healthy human PBMCs were exposed to lung associated components for 6 days. The cells were treated with surfactant (Infasurf®: 100 μg/ml), and cytokines (GM-CSF: 10 ng/ml, TGF-β: 5 ng/ml, IL-10: 5 ng/ml) every alternative day, or left untreated (UT-MDM). The whole cell lysate was made and Western blot was performed to check the expression of PPARG, PU.1, H3K4mel, and H3K4me3. Increased expression of PPARG, PU.1, H3K4mel and decreased expression of H3K4me3 show HAM like phenotype. FIG. 4 is a photographic image of Western blots of untreated MDM cells (UT-MDM) and AIL cells demonstrating HAM like phenotype. Actin was used as a loading control. Representative data showing the expression of indicated proteins from three human donors.

Figure 5A:
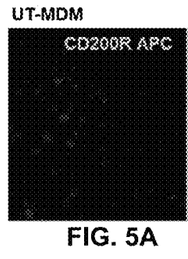
FIGS. 5A, 5F, and 5K are confocal microscopic images of UT-MDM and AML cells and isotype control cells, respectively, following immunohistochemistry using anti-CD200R (pink).
Figure 5B:
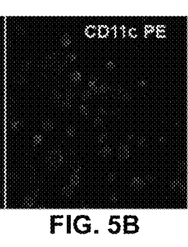
FIGS. 5B, 5G, and 5L are confocal microscopic images of UT-MDM and AML cells and isotype control cells, respectively, following immunohistochemistry using anti-CD11c (red).
Figure 5C:
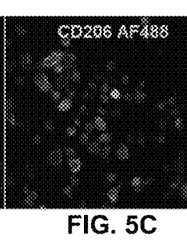
FIGS. 5C, 5H, and 5M are confocal microscopic images of UT-MDM and AML cells and isotype control cells, respectively, following immunohistochemistry using anti-CD206 (green).
Figure 5D:
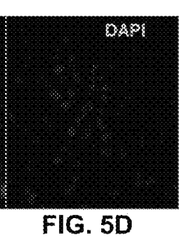
FIGS. 5D, 5I, and 5N are confocal microscopic images of UT-MDM and AML cells and isotype control cells, respectively, following immunohistochemistry using DAPI for nucleus (blue).
Figure 5E:
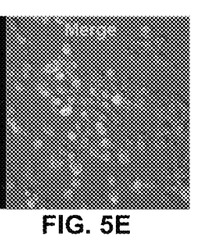
FIGS. 5E, 5J, and 5O are merged confocal microscopic images of UT-MDM and AML cells UT-MDM and AML cells and isotype control cells, respectively, following immunohistochemistry using anti-CD200R (pink), CD11c (red), CD206 (green), and DAPI for nucleus (blue). Scale bar: 20 µm and 40× magnification. Representative data showing the expression of indicated proteins from 2 human donors.
Figure 5F:
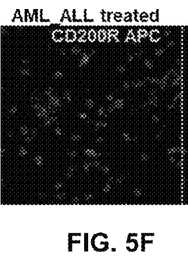
Figure 5G:
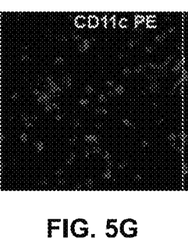
Figure 5H:
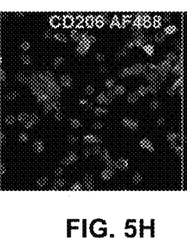
Figure 5I:
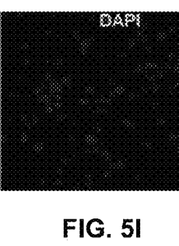
Figure 5J:
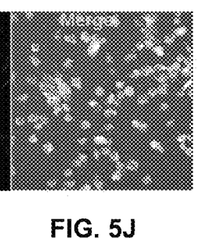
Figure 5K:
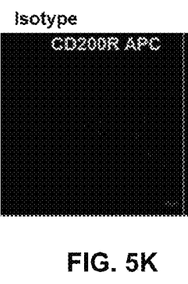
Figure 5L:
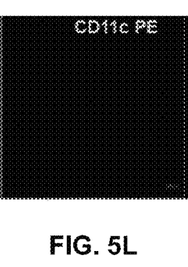
Figure 5M:
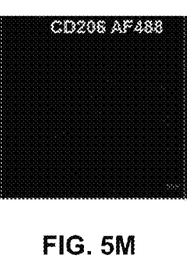
Figure 5N:
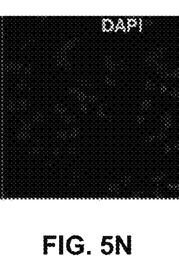
Figure 5O:
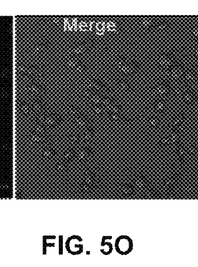

The AML cells were assessed for further HAM like phenotype. AML cells demonstrated HAM like phenotype, increased expression of CD200R, CD11c, CD206, CD163, and decreased expression of CD36, CD11 b as compare to MDM. Healthy human PBMCs were exposed to lung associated components for 6 days. The cells were treated with surfactant (Infasurf: 100 μg/mL), and cytokines (GM-CSF: 10 ng/mL, TGF-β: 5 ng/mL, IL-10: 5 ng/mL) every alternative day, or left untreated (UT-MDM). The cells were immunostained with anti-CD200R, CD11c, CD206, CD36, CD163, CD11b and DAPI for nucleus, and evaluated by confocal microscopy. FIGS. 5A, 5F, and 5K are confocal microscopic images of UT-MDM and AML cells and isotype control cells, respectively, following immunohistochemistry using anti-CD200R (pink). FIGS. 5B, 5G, and 5L are confocal microscopic images of UT-MDM and AML cells and isotype control cells, respectively, following immunohistochemistry using anti-CD11c (red). FIGS. 5C, 5H, and 5M are confocal microscopic images of UT-MDM and AML cells and isotype control cells, respectively, following immunohistochemistry using anti-CD206 (green). FIGS. 5D, 5I, and 5N are confocal microscopic images of UT-MDM and AML cells and isotype control cells, respectively, following immunohistochemistry using DAPI for nucleus. FIGS. 5E, 5J, and 5O are merged confocal microscopic images of UT-MDM and AML cells and isotype control cells, respectively, following immunohistochemistry using anti-CD200R (pink), CD11c (red), CD206 (green) and DAPI for nucleus (blue). Scale bar: 20 μm and 40× magnification. Representative data showing the expression of indicated proteins from 2 human donors.

Figure 6A:
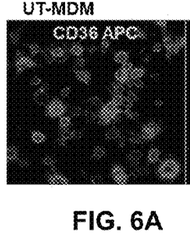
FIGS. 6A, 6F, and 6K are confocal microscopic images of UT-MDM and AML cells and isotype control cells, respectively following immunohistochemistry using anti-CD36 (pink).
Figure 6B:
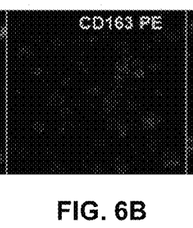
FIGS. 6B, 6G, and 6L are confocal microscopic images of UT-MDM and AML cells and isotype control cells, respectively, following immunohistochemistry using anti-CD163 (red).
Figure 6C:
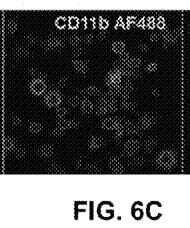
FIGS. 6C, 6H, and 6M are confocal microscopic images of UT-MDM and AML cells and isotype control cells, respectively, following immunohistochemistry using anti-CD11b (green).
Figure 6D:
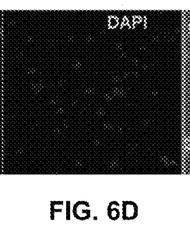
FIGS. 6D, 6I, and 6N are confocal microscopic images of UT-MDM and AML cells and isotype control cells, respectively, following immunohistochemistry using DAPI for nucleus (blue).
Figure 6E:
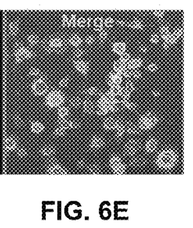
FIGS. 6E, 6J, and 6O are merged confocal microscopic images of UT-MDM and AML cells and isotype control cells, respectively, following immunohistochemistry using anti-CD36 (pink), CD163 (red), CD11b (green) and DAPI for nucleus (blue). Scale bar: 20 µm and 40× magnification. Representative data showing the expression of indicated proteins from 2 human donors.
Figure 6F:
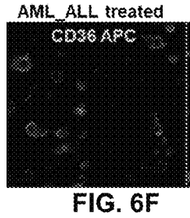
Figure 6G:
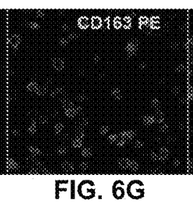
Figure 6H:
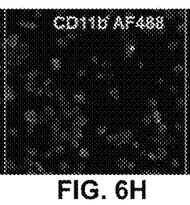
Figure 6I:
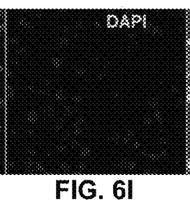
Figure 6J:
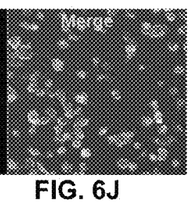
Figure 6K:
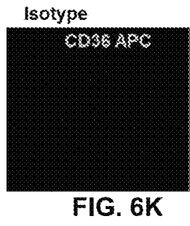
Figure 6L:
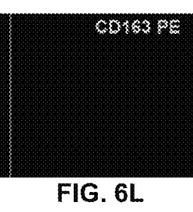
Figure 6M:
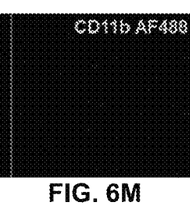
Figure 6N:
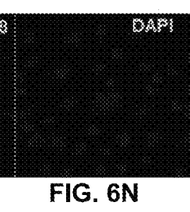
Figure 6O:
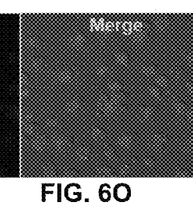

FIGS. 6A, 6F, and 6K are confocal microscopic images of UT-MDM and AML cells and isotype control cells, respectively, following immunohistochemistry using CD36 (pink). FIGS. 6B, 6G, and 6L are confocal microscopic images of UT-MDM and AML cells and isotype control cells, respectively, following immunohistochemistry using anti-CD163 (red). FIGS. 6C, 6II, and 6M are confocal microscopic images of UT-MDM and AML cells and isotype control cells, respectively, following immunohistochemistry using anti-CD11b (green). FIGS. 6D, 6I, and 6N are confocal microscopic images of UT-MDM and AML cells and isotype control cells, respectively, following immunohistochemistry using DAPI for nucleus (blue). FIGS. 6E, 6J, and 6O are merged confocal microscopic images of UT-MDM and AML cells and isotype control cells, respectively, following immunohistochemistry using anti-CD36 (pink), CD163 (red), CD11b (green) and DAPI for nucleus (blue). Scale bar: 20 μm and 40× magnification. Representative data showing the expression of indicated proteins from 2 human donors. Isotype control antibodies are used as a negative control as they match the exact host species, isotype, and subclass of the primary targeting antibody, but have no specificity to proteins present in the target organism or species.

Doing research on HAM is extremely difficult because these cells are only available from human donors by BAL or from recently deceased individuals. Also, HAM undergo rapid phenotypic changes during tissue culture cultivation. Thus, the field has been hampered in doing HAM research for decades. There have been attempts to create immortal cell lines from primary cells or to use stem cells but these have only achieved limited success. Using venipuncture to acquire blood-derived monocytes is a straightforward approach used by many labs around the world. One can cultivate these monocytes to create MDM but MDM do not share the unique feature of HAM. The systems and cell culture media described here enable the use of blood-derived monocytes to create HAM phenotypes (AML cells). Embodiments of the methods and systems to produce AML cells as disclosed here is considered a breakthrough for many fields of science and can be adopted for broad use.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein. To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

It is to be understood that the words which have been used are words of description rather than limitation, and that changes may be made within the purview of the appended claims without departing from the true scope and spirit of the embodiments in its broader aspects. While the embodiments have been described at some length and with some particularity with respect to certain aspects, it is not intended that the disclosure should be limited to any such particulars or embodiments or any particular embodiment, but it is to be construed with references to the appended claims.

What is claimed is:

1. A method of generating human alveolar macrophage-like (AML) cells in-vitro from human blood-derived monocytes, the method comprising:
   culturing a population of human blood-derived monocytes in a cell culture medium containing a mixture of a surfactant and two or more cytokines to generate the AML cells, wherein the human AML cells have increased expression of one or more of MRC1 (CD206), MARCO, MERTK, CES1, CD170, MCL1, CCL18, CXCL3, DUSP1, CXCL5, PU.1, H3K4me1, CD200R, CD11c, CD163, MCEMP1, and/or decreased expression of one or more of CD11b, CD36, MMP7, MMP9, H3K4me3 as compared to the human blood-derived monocytes.

2. The method of claim 1, wherein the surfactant is calfactant.

3. The method of claim 2, wherein the calfactant is present at about 100 μg/mL.

4. The method of claim 1, wherein the two or more cytokines are granulocyte-macrophage colony-stimulating factor (GM-CSF), transforming growth factor beta (TGF-β), and interleukin 10 (IL-10).

5. The method of claim 4, wherein the GM-CSF is present at about 10 ng/mL, the TGF-β is present at about 5 ng/mL, and the IL-10 is present at about 5 ng/mL.

6. A method of generating human alveolar macrophage-like (AML) cells in vitro from human blood-derived monocytes, the method comprising:
   culturing a population of the human blood-derived monocytes in a cell culture medium comprising a mixture of calfactant, granulocyte-macrophage colony-stimulating factor, transforming growth factor beta, and interleukin 10 to generate the AML cells.

7. The method of claim 6, wherein the human AML cells have increased expression of one or more of MRC1 (CD206), MARCO, MERTK, CES1, CD170, MCL1, CCL1), CXCL3, DUSP1, CXCL5, PU.1, H3K4me1, CD200R, CD11c, CD163, MCEMP1, and/or decreased expression of one or more of CD11b, CD36, MMP7, MMP9, H3K4me3 as compared to the human blood-derived monocytes.

8. The method of claim 6, wherein the calfactant is present at about 100 μg/mL.

9. The method of claim 6, wherein the GM-CSF is present at about 10 ng/mL, the TGF-β is present at about 5 ng/mL, and the IL-10 is present at about 5 ng/mL.

* * * * *